United States Patent
Baxter et al.

[11] Patent Number: 6,102,905
[45] Date of Patent: Aug. 15, 2000

[54] PHOTOTHERAPY DEVICE INCLUDING HOUSING FOR AN OPTICAL ELEMENT AND METHOD OF MAKING

[75] Inventors: Lincoln S. Baxter, Centerville; Edward L. Sinofsky, Dennis; Norman Farr, Monument Beach, all of Mass.

[73] Assignee: CardioFocus, Inc., West Yarmouth, Mass.

[21] Appl. No.: 09/040,600

[22] Filed: Mar. 18, 1998

Related U.S. Application Data

[63] Continuation-in-part of application No. 08/827,631, Apr. 10, 1997, Pat. No. 5,908,415, which is a continuation of application No. 08/303,605, Sep. 9, 1994, abandoned.

[51] Int. Cl.$^7$ ................................................ A61R 7/00
[52] U.S. Cl. .............................. 606/15; 606/16; 606/7
[58] Field of Search ........................ 606/7, 10, 13–17; 607/88–90

[56] References Cited

U.S. PATENT DOCUMENTS

| | | | |
|---|---|---|---|
| 4,269,648 | 5/1981 | Dakss et al. | 156/293 |
| 4,648,892 | 3/1987 | Kittrell et al. | 606/7 |
| 4,718,417 | 1/1988 | Kittrell et al. | 128/303.1 |
| 4,817,601 | 4/1989 | Roth et al. | 128/303.1 |
| 4,852,567 | 8/1989 | Sinofsky | 128/303.1 |
| 5,068,515 | 11/1991 | van den Bergh et al. | 219/121.73 |
| 5,093,877 | 3/1992 | Aita et al. | 385/34 |
| 5,167,686 | 12/1992 | Wong | 65/4.21 |
| 5,231,684 | 7/1993 | Narciso, Jr. et al. | 385/80 |
| 5,466,234 | 11/1995 | Loeb et al. | 606/7 |
| 5,476,461 | 12/1995 | Cho et al. | 606/15 |
| 5,534,000 | 7/1996 | Bruce | 606/15 |
| 5,571,099 | 11/1996 | Purcell, Jr. et al. | 606/17 |
| 5,717,807 | 2/1998 | Theroux et al. | 606/15 |
| 5,728,091 | 3/1998 | Payne et al. | 606/15 |
| 5,782,825 | 7/1998 | Anderson | 606/15 |
| 5,868,734 | 2/1999 | Soufiane et al. | 606/15 |

FOREIGN PATENT DOCUMENTS

WO 96/07451  3/1996  WIPO .

*Primary Examiner*—Robert L. Nasser
*Attorney, Agent, or Firm*—Thomas J. Engellenner; Nutter, McClennen & Fish, LLP

[57] ABSTRACT

A phototherapy device which can include an optical fiber having a perfluorinated polymer outer buffer coating, and an optical element, such as a GRIN lens or a mirror, disposed at its distal end. A tubular housing encases the optical element and is thermally bonded to at least a portion of the buffer. The component elements of the device can be constructed of materials having similar thermal characteristic to inhibit the effect of heat cycling on the device. In addition, the materials of the device, and in particular the housing, can be selected to inhibit wear and scrapping of the lumen of the delivery instrument during use. A marker band can be positioned about the optical fiber to facilitate viewing of the phototherapy device in-vivo.

20 Claims, 4 Drawing Sheets

PHOTOTHERAPY DEVICE INCLUDING HOUSING FOR AN OPTICAL ELEMENT AND METHOD OF MAKING

REFERENCE TO RELATED APPLICATIONS

This application is a continuation-in-part of U.S. patent application Ser. No. 08/827,631, now U.S. Pat. No. 5,908,415 incorporated herein by reference and filed Apr. 10, 1997, which is a file-wrapper continuation of U.S. patent application Ser. No. 08/303,605, incorporated herein by reference and filed Sep. 9, 1994 now abandoned.

BACKGROUND OF THE INVENTION

The technical field of this invention is phototherapy and, in particular, instruments employing optical fibers or other flexible waveguides to deliver radiation to a targeted biological site.

Fiber optic phototherapy is an increasingly popular modality for the diagnosis and/or treatment of a wide variety of diseases. For example, in surgery, infrared laser radiation will often be delivered to a surgical site via a hand-held instrument incorporating an optically transmissive fiber in order to coagulate blood or cauterize tissue. Other uses for optical fiber-delivered radiation include treatment of artheroscerotic disease and prostatic disease. U.S. Pat. No. 4,878,492 issued to Sinofsky et al., incorporated herein by reference, discloses the use of infrared radiation to heat blood vessel walls during balloon angioplasty in order to fuse the endothelial lining of the blood vessel and seal the surface. Another application of fiber-delivered radiation is disclosed in U.S. Pat. No. 5,053,033 (Clarke), incorporated herein by reference. Clarke teaches that retenosis following angioplasty can be inhibited by application of U.V. radiation to the angioplasty site to kill smooth muscle cells which would other wise proliferate in response to angioplasty-induced injuries to blood vessel walls.

Optical fiber-delivered radiation has further been used to treat prostate enlargement caused by Benign Prostate Hyperplasia (BPH) or prostate cancer. Such treatments include delivering the optical fiber transurethrally or hypodermically to apply therapeutic temperatures to the enlarged prostatic tissue.

Moreover, fiber optic delivery systems have been incorporated in endoscopic or catheter-based instruments to deliver radiation to a targeted biological site from within a body lumen or cavity. Typically, the fiber optic phototherapy device is inserted through an instrument lumen or catheter for delivery in-vivo.

Conventional optical fiber phototherapy devices can include an optical element, such as a focusing lens, that is coupled to the optical fiber by a cylindrical housing. The housing is typically a metallic band or cuff, constructed from stainless steel or gold, that is sized to hold both the lens and the optical fiber in a friction-tight fit. Alternatively, the housing can be glued to the optical fiber or can be threaded to facilitate connection to the fiber.

The performance of such conventional phototherapy devices incorporating a metallic housing has proven less than optimal for a number of reasons. In particular, when the phototherapy device is placed within the lumen of the delivery instrument for insertion into the patient, the metallic housing can scrape against the inner walls of the delivery instrument lumen and cause damage to the lumen.

Additional problems associated with such conventional phototherapy devices include loosening of the optical element due to thermal cycling, as the metallic housing and the optical element, as well as the optical fiber, have significantly different thermal characteristics, such as the coefficient of thermal expansion. Thus, during the application of radiation, the housing tends to expand greater than both the optical fiber and the optical element, resulting in loosening of the connection between the housing, the optical fiber and optical element. Thermal cycling can also result from sterilization procedures and during shipping of the phototherapy device.

Moreover, the effects of thermal cycling are magnified by the presence of the metallic housing which can absorb significant amounts of radiation from the optical fiber thereby further increasing the temperature of the housing. For example, a stainless steel housing can absorb approximately 40% of the incident radiation.

As the above described optical fiber phototherapy devices have proven less than optimal, it is an object of the present invention to provide improved phototherapy devices having a construction that permits insertion into the lumen of a delivery instrument without causing damage or significant wear to the lumen.

Another object of the present invention is to provide a phototherapy device including components parts constructed of materials chosen to reduce wear on the lumen of the delivery instrument.

Still another object of the present invention is to provide phototherapy devices including component parts having a similar thermal characteristics to inhibit the effects of heat cycling.

A further object of the present invention is to provide phototherapy devices that are simple and inexpensive to manufacture.

Another object of the present invention is to provide an improved method of making a phototherapy device.

Other general and more specific objects of this invention will in part be obvious and will in part be evident from the drawings and the description which follow.

SUMMARY OF THE INVENTION

These and other objects of the present invention are attained by the phototherapy devices of the present invention which include an optical fiber having a surrounding buffer coating, and having an optical element which is optically coupled to the fiber and disposed at its distal end. The phototherapy device of the present invention further includes a tubular housing encasing the optical element and bonded to at least a portion of the buffer. A significant advantage of the present invention over prior art devices is that bond between the housing and the buffer is substantially impervious to thermal cycling. Thus, by bonding the housing directly to the buffer, the effects of thermal stress that can cause loosening of the housing from the buffer are inhibited. In a preferred embodiment, the housing is thermally bonded to the buffer.

According to one aspect of the present invention, both the fiber buffer and the housing can be made of a perfluorinated polymer. The perfluorinated polymer of the housing and the buffer can be such perfluorinated polymers as ethylene tetrafluoroethylene (ETFE), polytetrafluoroethylene (PTFE), perfluorinated ethylenepropylene (FEP), and perfluoroalkoxy fluorocarbon resin (PFA). A significant advantage of the present invention over the prior devices is that the housing is constructed from a perfluorinated polymer, a softer material than metal, to reduce wear on and inhibit scrapping of the lumen of the delivery instrument.

According to a preferred embodiment of the invention, the housing is made from a material having a coefficient of thermal expansion approximately equal to the coefficient of thermal expansion of the buffer. In this manner, both the housing and the buffer will thermally expand (and contract) approximately the same amount, thus minimizing the effects of heat cycling on the device.

According to a further aspect of the present invention, the optical element can be thermally bonded or glued to the housing. In the alternative, the housing can be heat shrunk about the optical element to hold the optical element in a friction-tight fit. The optical element can be a GRIN lens or a mirror. Preferably, the optical element serves to receive the radiation propagating through the fiber and transmit the radiation in a predefined pattern to a target tissue region.

According to another aspect of the invention, the optical element can be constructed of a perfluorinated polymer material and formed in the shape of a cylindrical disk or a hemispherical dome.

In a preferred embodiment of the invention, the device includes a marker band positioned about the optical fiber or buffer to facilitate viewing the phototherapy device in-vivo. The band is preferably visible under fluoroscopy. In addition, the band is preferably made of gold and can be welded to the optical fiber or, alternatively, embedded in the buffer.

A preferred method of the present invention for making a phototherapy device includes the steps of providing an optical fiber with a perfluorinated polymer buffer coating and attaching an optical element to a distal end of the optical fiber. The optical element can be attached to the distal end of the fiber by encasing the optical element in a housing and bonding the housing to at least a portion of the buffer. Preferably, the housing is thermally bonded to the buffer.

According to one aspect of the present invention, the step of attaching the optical element can further include the step of molding the housing from a perfluorinated polymer. The perfluorinated polymer of the housing is preferably selected from the group consisting of ethylene tetrafluoroethylene (ETFE), polytetrafluoroethylene (PTFE), perfluorinated ethylene-propylene (FEP), and perfluoroalkoxy fluorocarbon resin (PFA).

According to a further aspect of the present invention, the method can include the step of positioning a marker band about the optical fiber to facilitate viewing the phototherapy device in-vivo. In a preferred embodiment, the step of positioning the marker band further includes the step of embedding marker band within the buffer.

BRIEF DESCRIPTION OF THE DRAWING

These and other features and advantages of the present invention will be more fully understood by reference to the following detailed description in conjunction with the attached drawings in which like reference numerals refer to like elements through the different views. The drawings illustrate principles of the invention and, although generally or occasionally not to scale, may show relative dimensions.

DETAILED DESCRIPTION

Figure 1:
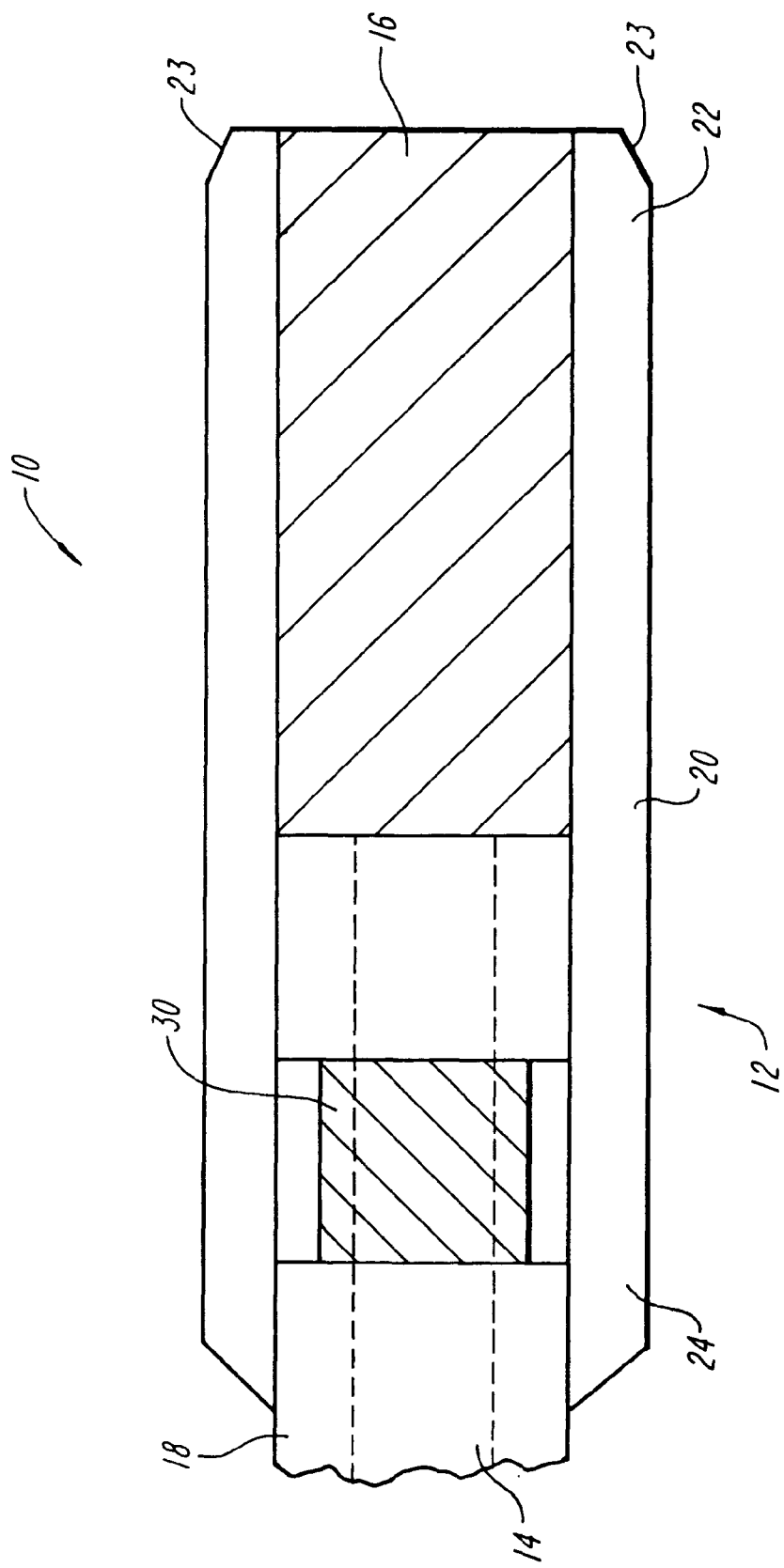
FIG. 1 is a side elevational view in cross-section of the distal end of a phototherapy device according to the teachings of the present invention.

The distal end 12 of a phototherapy device 10 useful for the treatment of a targeted tissue region in-vivo is illustrated in FIG. 1. The device includes an optical fiber 14 having an optical element 16 disposed at its distal end and an outer buffer coating 18. A tubular housing 20 encases the optical element 16 and is bonded to at least a portion of the buffer 18. The device 10 is preferably used in conjunction with a delivery instrument, such as a catheter, the working channel of a cystoscope, or the lumen of a hypodermic needle, to facilitate delivery of the device 10 proximate the targeted tissue region for phototherapy.

The terms "delivery instrument" as used herein is intended to broadly encompass various instruments which can be passed through body lumens of various kinds, sizes, and shapes or, in the alternative, can be passed hypodermically through the patient's skin.

The outer buffer coating 18 is concentricly disposed about the optical fiber 14 and is preferably constructed of a perfluorinated polymer material, such as TEFLON® copolymers (sold by DuPont, Wilmington, Del.). Suitable perfluorinated polymers include polytetrafluoroethylene (PTFE) sold under the trademark TEFLON by DuPont; ethylene tetrafluoroethylene (ETFE), sold under the trademark TEFZEL by DuPont; perfluorinated ethylene-propylene (FEP), sold under the trademark TEFLON FEP by DuPont; and perfluoroalkoxy fluorocarbon resin (PFA), sold under the trademark TEFLON PFA. Optical fibers with such coatings are commercially available from a variety of sources, such as Spectran Specialty Optics Co. Inc. (Avon, Conn.).

As illustrated in FIG. 1, the housing 20 is cylindrical in shape and includes a distal end 22 and a proximal end 24. The distal end 22 of the housing 20 is sized to receive the optical element 16 and includes a tapered end portion 23 to facilitate insertion of the device into the lumen of the delivery instrument. Accordingly, the inner diameter of the distal end 22 is preferably greater than the outer diameter of the optical element 16. In a preferred embodiment, the optical element 16 can be secured within the housing 20 by heat shrinking the housing 20 about the optical element. In this manner, the optical element 20 can be held in a friction-tight fit.

Figure 2:
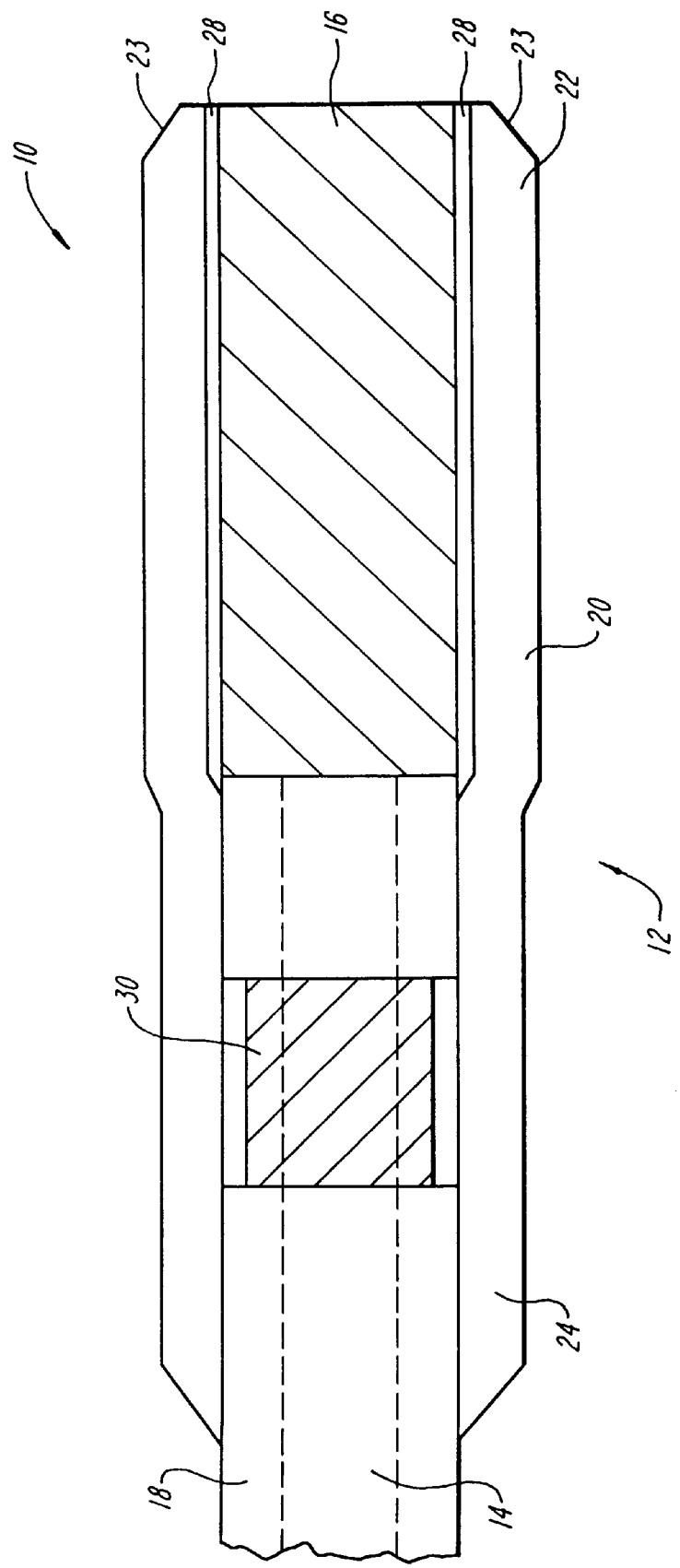
FIG. 2 is a side elevational view in cross-section of the distal end of the phototherapy device of FIG. 1, illustrating the optical element secured to the housing by an adhesive according to the teachings of the present invention.

In the alternative, a glue or other adhesive 28 can be used to secure the optical element 16 to the distal end 22 of the housing 20, as illustrated in FIG. 2. In a preferred embodiment, the adhesive is a U.V. curing glue, such as LOCTITE 3211 (available from Loctite, of Rocky Hill, Conn.). The diameter of the distal end 22 of the housing 20 can be increased to accommodate the adhesive layer 28.

Figure 4:
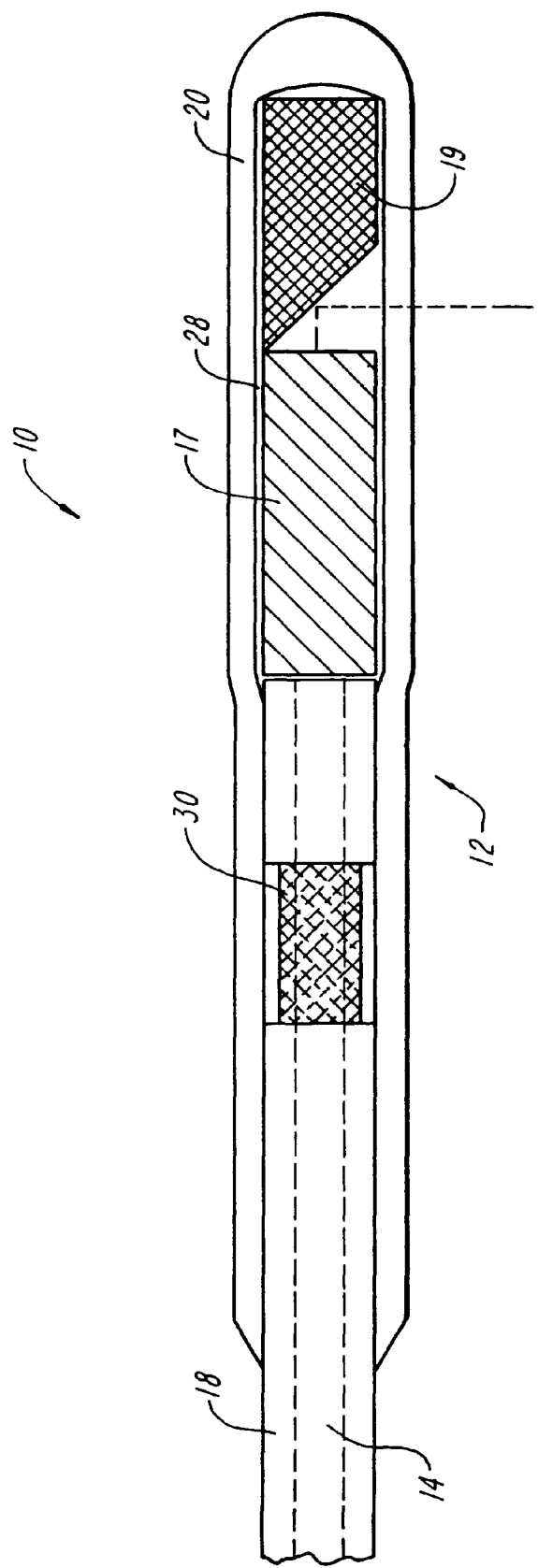
FIG. 4 is a side elevational view in cross-section of the distal end of an alternative embodiment of the phototherapy device of the present invention, in which the optical element includes a lens and a mirror according to teachings of the present invention.

Referring to FIGS. 1 and 2, the optical element 16 can be, for example, a graded index (GRIN) lens (available from NSG America Inc., Somerset, N.J.) for focusing or collimating irradiation propagated along the length optical fiber 14. In the alternative, the optical element 16 can be a mirror for reflecting irradiation back through a diffusive tip attached to distal end of the optical fiber, as is known for phototherapy devices configured for "sideways-emitting"

radiation. As illustrated in FIG. 4, the optical element can also include both a lens 17, such as a GRIN lens, and a mirror 19. A sideways emitting phototherapy device is described in commonly owned U.S. patent application Ser. No. 08/827,631, which is incorporated herein by reference.

Continuing to refer to FIGS. 1 and 2, the optical element 16 alternatively can be a cylindrical disk formed from a perfluorinated polymer material such as TEFLON® copolymers (sold by DuPont). Suitable perfluorinated polymers include polytetrafluoroethylene (PTFE) sold under the trademark TEFLON by DuPont; ethylene tetrafluoroethylene (ETFE), sold under the trademark TEFZEL by DuPont; perfluorinated ethylene-propylene (FEP), sold under the trademark TEFLON FEP by DuPont; and perfluoroalkoxy fluorocarbon resin (PFA), sold under the trademark TEFLON PFA. The TEFLON® copolymer cylindrical disk allows the irradiation propagating along the length of the optical fiber 14 to emerge from the disk as a generally diverging irradiation beam, without effecting scattering of the irradiation beam.

Figure 3:
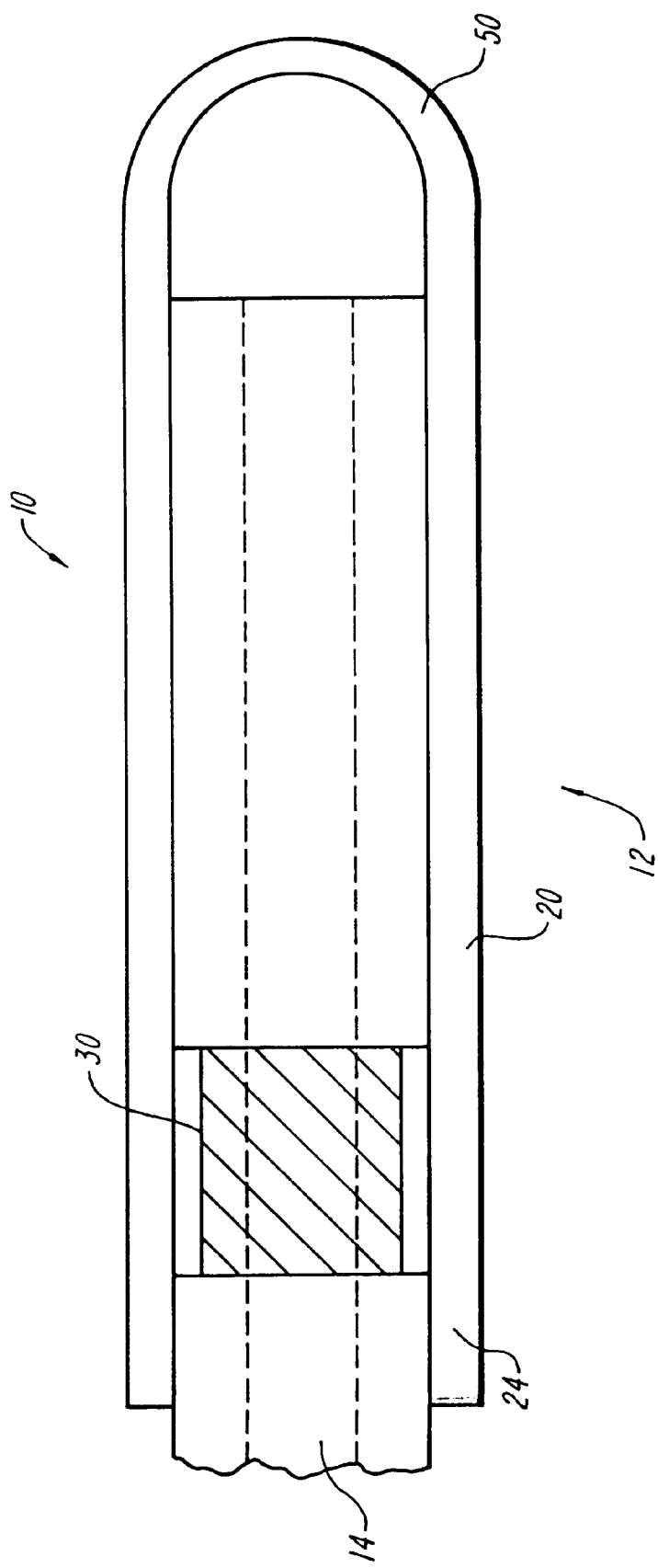
FIG. 3 is a side elevational view in cross-section of the distal end of an alternative embodiment of the phototherapy device of the present invention, in which the optical element is a perfluorinated polymer dome according to the teachings of the present invention.

In an alternative embodiment, the optical element 16 can be a hemispherical-dome 50 constructed from a perfluorinated polymer material such as TEFLON® polymers (sold by DuPont), as illustrated in FIG. 3. Suitable perfluorinated polymers include polytetrafluoroethylene (PTFE) sold under the trademark TEFLON by DuPont; ethylene tetrafluoroethylene (ETFE), sold under the trademark TEFZEL by DuPont; perfluorinated ethylene-propylene (FEP), sold under the trademark TEFLON FEP by DuPont; and perfluoroalkoxy fluorocarbon resin (PFA), sold under the trademark TEFLON PFA. The TEFLON® copolymer hemispherical dome 50 allows the irradiation propagating along the length of the optical fiber 14 to expand as the irradiation emerges from the disk, providing a generally frusto-conically shaped beam profile, without effecting scattering of the irradiation beam. The hemispherical dome 50 can be coupled to the distal end 22 of the housing 20 by thermal bonding. In this manner, the housing 20 and the dome 50 form a TEFLON(® copolymer cap that fits over the distal end of the phototherapy device 10.

The proximal end 24 of the housing 20 is preferably sized to receive the distal end of the optical fiber 14 such that the housing 20, and the optical element 16, can be coupled to the optical fiber. Accordingly, the inner diameter of the proximal end 24 of the housing 20 is preferably greater than the outer diameter of the outer buffer coating 18. The proximal end 24 of the housing 20 is preferably thermally bonded to the outer buffer coating 18 to thereby connect the housing 20 to the distal end of the optical fiber 14.

The housing 20 is preferably constructed of a biocompatable material having a similar thermal characteristics, i.e., melting temperature and/or coefficient of thermal expansion, as both the outer buffer layer 18 and the optical element 16. This allows the housing 20 to react to the effects of heat cycling in a manner similar to both the buffer 18 and the optical element 16. In particular, the housing 20 can thermally expand (and contract) at a rate and in an amount approximately equal to that of the buffer and the optical element to thereby inhibit weakening of the connection between the elements due to thermal cycling.

In addition, the housing 20 is preferably constructed of a material that is sufficiently "soft" and lubricious so as to inhibit scrapping of the lumen of the delivery instrument during insertion while concomitantly having sufficient strength to maintain the optical element 20 in connection with the optical fiber 14.

Housing materials exhibiting the above described preferred characteristics include perfluorinated polymers such as TEFLON® copolymers (sold by DuPont). Suitable perfluorinated polymers include polytetrafluoroethylene (PTFE) sold under the trademark TEFLON by DuPont; ethylene tetrafluoroethylene (ETFE), sold under the trademark TEFZEL by DuPont; perfluorinated ethylene-propylene (FEP), sold under the trademark TEFLON FEP by DuPont; and perfluoroalkoxy fluorocarbon resin (PFA), sold under the trademark TEFLON PFA.

Thermal bonding is preferably effected at a temperature sufficient to cause flowing of the perfluorinated materials of the housing and the outer buffer coating without causing bubbling of the material. Accordingly, the preferred temperature is near the melting temperature of the perfluorinated material selected for use.

In a preferred embodiment of the present invention, the phototherapy device 10 includes an annular marker band 30 positioned about the optical fiber 14 to facilitate viewing of the phototherapy device in-vivo. The marker band 30 is preferably made from gold. The band 30 can be welded to the optical fiber 14 or buffer 18 or, alternatively, can be embedded within the buffer 18 (e.g., wrapped around the fiber in a location where the buffer has been partially or completely stripped away).

An exemplary phototherapy device was constructed according to the teachings of the present invention having a housing constructed from ETFE. A GRIN lens was encased within the distal end of the housing and held in a friction-tight fit. A portion of the outer buffer was stripped away from the optical fiber to accommodate placement of the marker band about the optical fiber. The proximal end of the housing was then positioned over the distal end of the optical fiber. Heat was then applied to the housing to heat shrink the housing about the buffer, and the GRIN lens, and thermally bond the housing to the outer buffer coating thereby serving to optically align the fiber and lens together. Thermal bonding was accomplished at approximately 500° F.

The materials and configuration of the phototherapy device of the present invention permits insertion into of the device into the lumen of a delivery instrument without causing scraping or significant wear to the lumen. In particular, the housing for coupling the optical element to the optical fiber is constructed of materials chosen to reduce wear on and inhibit scraping of the lumen of the delivery instrument during use. In addition, the materials of the housing are chosen to have similar thermal characteristics to that of the outer buffer coating and the optical element to inhibit the effects of heat cycling on the device.

Moreover, the materials of the housing are chosen to reduce the amount of radiation absorbed by the housing, thus reducing the amount of heating of the housing, as well as the amount of heat that is transferred to the lumen of the delivery instrument. Accordingly, for a given radiation intensity, the housing of the phototherapy device of the present invention is "cooler" than that of prior art phototherapy devices.

Moreover, in the embodiments of the phototherapy device in which the optical element is constructed from a TEFLON® copolymer, the housing, the outer buffer coating, and the optical element can be formed from the same copolymer, such as ETFE. In this manner, the thermal characteristics of these elements will be substantially identical, thus further inhibiting the effects of heat cycling on the device.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. A phototherapy device, comprising:
   an optical fiber;
   a buffer coating the optical fiber, the buffer being formed from a perfluorinated polymer material;
   a tubular housing thermally bonded to at least a portion of the buffer, the housing being formed from a perfluorinated polymer material, wherein the coefficient of thermal expansion of the housing is approximately equal to the coefficient of thermal expansion of the buffer such that the housing and buffer will expand at substantially the same rate, thereby reducing the effects of thermal cycling on the device; and
   a discrete optical element at least partly encased in the housing in optical alignment with the optical fiber, the optical element being formed from a perfluorinated polymer material.

2. The phototherapy device according to claim 1, wherein the perfluorinated polymer of the housing is selected from the group consisting of ethylene tetrafluoroethylene (ETFE), polytetrafluoroethylene (PTFE), perfluorinated ethylene-propylene (FEP), and perfluoroalkoxy fluorocarbon resin (PFA).

3. The phototherapy device according to claim 1, wherein the optical element is thermally bonded to the housing.

4. The phototherapy device according to claim 1, wherein the optical element is a GRIN lens.

5. The phototherapy device according to claim 4, further comprising a mirror for reflecting radiation from the GRIN lens, the mirror being encased by the tubular housing.

6. The phototherapy device according to claim 1, further comprising a marker band positioned about the optical fiber to facilitate viewing the phototherapy device in-vivo.

7. The phototherapy device according to claim 6, wherein the band is welded to the optical fiber.

8. The phototherapy device according to claim 6, wherein the band is made of gold.

9. The phototherapy device according to claim 6, wherein the band is embedded in the buffer.

10. The phototherapy device according to claim 9, wherein the housing is thermally bonded about the buffer to secure the band to the optical fiber.

11. The phototherapy device according to claim 1, wherein the optical element is a cylindrical disk.

12. The phototherapy device according to claim 1, wherein the optical element is a hemispherical dome.

13. The phototherapy device according to claim 1, wherein the buffer, the housing and the optical element are formed from the same polymer.

14. A method of making a phototherapy device comprising the steps of:
    providing a perfluorinated polymer buffer about an optical fiber,
    attaching a perfluorinated polymer optical element to a distal end of the optical fiber by encasing the optical element in a perfluorinated polymer housing, and
    thermally bonding the housing to at least a portion of the buffer such that the housing and buffer will expand at substantially the same rate, thereby reducing the effects of thermal cycling on the device.

15. The method according to claim 14, wherein the step of attaching the optical element further comprises the step of molding the housing.

16. The method according to claim 15, wherein the perfluorinated polymer of the housing is selected from the group consisting of ethylene tetrafluoroethylene (ETFE), polytetrafluoroethylene (PTFE), perfluorinated ethylene-propylene (FEP), and perfluoroalkoxy fluorocarbon resin (PFA).

17. The method according to claim 14, further comprising the step of positioning a marker band about the optical fiber to facilitate viewing the phototherapy device in-vivo.

18. The method according to claim 17, wherein the step of positioning the marker band further comprises the step of embedding marker band within the buffer.

19. A phototherapy device comprising:
    an optical fiber having a distal end,
    a perfluorinated polymer buffer coating concentric about said optical fiber,
    a perfluorinated polymer optical element optically coupled to the distal end of the optical fiber, and
    a perfluorinated polymer housing encasing the optical element and thermally bonded to at least a portion of the buffer such that the housing and buffer will expand at substantially the same rate, thereby reducing the effects of thermal cycling on the device.

20. The phototherapy device according to claim 13, wherein the polymer is ETFE.

* * * * *